(12) United States Patent
Anderson et al.

(10) Patent No.: US 8,097,031 B2
(45) Date of Patent: Jan. 17, 2012

(54) WARMING DEVICE WITH PROVISIONS FOR DEPLOYING ELEMENTS OF AN UPPER BODY CONVECTIVE APPARATUS AND FOR DEPLOYING THE LOWER PORTION OF THE WARMING DEVICE

(75) Inventors: Thomas P. Anderson, Savage, MN (US); Carol J. Panser, St. Louis Park, MN (US)

(73) Assignee: Arizant Healthcare Inc., Eden Prairie, MN (US)

( * ) Notice: Subject to any disclaimer, the term of this patent is extended or adjusted under 35 U.S.C. 154(b) by 472 days.

(21) Appl. No.: 12/386,243

(22) Filed: Apr. 15, 2009

(65) Prior Publication Data
US 2009/0228083 A1    Sep. 10, 2009

Related U.S. Application Data

(63) Continuation-in-part of application No. 11/583,432, filed on Oct. 19, 2006, now Pat. No. 7,819,911, and a continuation-in-part of application No. 11/583,477, filed on Oct. 19, 2006, now Pat. No. 7,871,429, and a continuation-in-part of application No. 11/583,480, filed on Oct. 19, 2006, now Pat. No. 7,914,566, and a continuation-in-part of application No. 11/583,481, filed on Oct. 19, 2006, now Pat. No. 7,857,841.

(60) Provisional application No. 60/729,000, filed on Oct. 20, 2005, provisional application No. 60/835,602, filed on Aug. 4, 2006.

(51) Int. Cl.
*A61F 7/00* (2006.01)
(52) U.S. Cl. .......................... 607/108; 607/104; 607/114
(58) Field of Classification Search .................. 607/104, 607/108, 112, 114
See application file for complete search history.

(56) References Cited

U.S. PATENT DOCUMENTS
2,512,559 A    6/1950    Williams .......................... 5/347
(Continued)

FOREIGN PATENT DOCUMENTS
FR            821150       11/1937
(Continued)

OTHER PUBLICATIONS

P.O. Fanger, Thermal Comfort: Analysis and Applications in Environmental Engineering, Danish Technical Press, 1970, pp. 5-67.

(Continued)

*Primary Examiner* — Roy Gibson
(74) *Attorney, Agent, or Firm* — Terrance A. Meador; Incaplaw

(57) ABSTRACT

A warming device includes a clinical garment having an inside surface supporting one or more convective apparatuses disposed to warm a patient perioperatively. The warming device may include an upper body convective apparatus supported on the inside of the clinical garment between its sleeves. The construction of the upper body convective apparatus includes pulling elements that draw folded components of the apparatus from sleeves of the clinical garment when pulled. The warming device may include a multi-section convective apparatus disposed longitudinally in a lower portion of the clinical garment and having separately inflatable sections, each for enabling a particular mode of warming. The construction of the multi-section convective apparatus includes a therapeutic warming section with an inlet port positioned for convenient and safe access when the lower portion of the warming device is disposed to drape over the lower limbs of a person while the therapeutic warming section is being operated.

29 Claims, 9 Drawing Sheets

U.S. PATENT DOCUMENTS

| | | | |
|---|---|---|---|
| 2,573,414 A | 10/1951 | Dunn | 128/144 |
| 2,826,758 A | 3/1958 | Kahn | 2/61 |
| 3,468,299 A | 9/1969 | D'Amato | 126/204 |
| 3,610,323 A | 10/1971 | Troyer | 165/46 |
| 3,757,366 A | 9/1973 | Sacher | 5/347 |
| 3,855,635 A | 12/1974 | Ramirez | 2/114 |
| 3,911,499 A | 10/1975 | Benevento et al. | 2/114 |
| 3,950,789 A | 4/1976 | Konz et al. | 2/93 |
| 4,055,173 A | 10/1977 | Knab | 128/139 |
| 4,146,933 A | 4/1979 | Jenkins et al. | 2/2 |
| 4,369,528 A | 1/1983 | Vest et al. | 2/69 |
| 4,494,248 A | 1/1985 | Holder | 2/69 |
| 4,524,463 A | 6/1985 | Ogden | 2/105 |
| 4,558,468 A | 12/1985 | Landry et al. | 2/51 |
| 4,578,825 A | 4/1986 | Vote | 2/114 |
| 4,587,671 A | 5/1986 | Rodriguez et al. | 2/69 |
| 4,651,727 A | 3/1987 | Howorth | 128/201.3 |
| 4,653,120 A | 3/1987 | Leaf | 2/114 |
| 4,696,066 A | 9/1987 | Ball et al. | 2/272 |
| 4,718,124 A | 1/1988 | Sawicki et al. | 2/114 |
| 4,787,101 A | 11/1988 | Feinberg | 2/105 |
| 4,914,752 A | 4/1990 | Hinson et al. | 2/2 |
| 4,964,282 A | 10/1990 | Wagner | 62/259.3 |
| 5,062,424 A | 11/1991 | Hooker | |
| 5,190,031 A | 3/1993 | Guibert et al. | 128/399 |
| 5,255,390 A | 10/1993 | Gross et al. | |
| 5,304,213 A | 4/1994 | Berke et al. | 607/104 |
| 5,360,439 A | 11/1994 | Dickerhoff et al. | 607/104 |
| 5,367,710 A | 11/1994 | Karmin | 2/114 |
| 5,411,541 A | 5/1995 | Bell et al. | 607/104 |
| 5,443,488 A | 8/1995 | Namemye et al. | 607/104 |
| 5,572,742 A | 11/1996 | McFadden | 2/114 |
| 5,575,006 A | 11/1996 | Wolfe | 2/114 |
| 5,611,087 A | 3/1997 | Adkins | 2/114 |
| 5,620,482 A | 4/1997 | Augustine et al. | 607/107 |
| 5,697,963 A | 12/1997 | Augustine | 607/108 |
| 5,733,318 A | 3/1998 | Augustine | 607/104 |
| 5,749,109 A | 5/1998 | Kappel | 5/423 |
| 5,785,716 A | 7/1998 | Bayron | 607/108 |
| 5,891,187 A | 4/1999 | Winthrop et al. | 607/96 |
| 5,946,722 A | 9/1999 | Trautmann | 2/83 |
| 5,970,519 A | 10/1999 | Weber | 2/81 |
| 5,974,605 A | 11/1999 | Dickerhoff et al. | 5/421 |
| 6,049,907 A | 4/2000 | Palomo | 2/51 |
| 6,154,883 A | 12/2000 | Spann et al. | 2/69 |
| 6,156,058 A | 12/2000 | Kappel et al. | 607/107 |
| 6,203,567 B1 | 3/2001 | Augustine | 607/104 |
| 6,216,270 B1 | 4/2001 | Moquin et al. | 2/69 |
| 6,235,019 B1 | 5/2001 | McAmish et al. | 442/79 |
| 6,378,136 B2 | 4/2002 | Matsushita | 2/114 |
| 6,484,321 B1 | 11/2002 | Shamam | 2/114 |
| 6,511,501 B1 | 1/2003 | Augustine et al. | 607/96 |
| 6,524,332 B1 | 2/2003 | Augustine et al. | 607/107 |
| 6,551,347 B1 | 4/2003 | Elkins | 607/104 |
| 6,571,574 B1 | 6/2003 | Blackstone | 62/420 |
| 6,596,019 B2 | 7/2003 | Turner et al. | 607/108 |
| 6,647,552 B1 | 11/2003 | Hogan | 2/114 |
| 6,694,522 B1 | 2/2004 | Neal | 2/114 |
| 6,792,622 B2 | 9/2004 | Graves | 2/114 |
| 6,799,332 B2 | 10/2004 | Hatton | 2/114 |
| 6,820,622 B1 | 11/2004 | Teves et al. | 128/849 |
| 6,851,125 B2 | 2/2005 | Fujikawa et al. | 2/51 |
| 6,876,884 B2 | 4/2005 | Hansen et al. | 607/104 |
| 7,001,416 B2 | 2/2006 | Augustine et al. | 607/104 |
| 7,226,454 B2 | 6/2007 | Albrecht et al. | 607/104 |
| 7,276,076 B2 | 10/2007 | Bieberich | 607/108 |
| 7,364,584 B2 | 4/2008 | Anderson | 607/108 |
| 7,470,280 B2 | 12/2008 | Bieberich | 607/104 |
| 2003/0126668 A1 | 7/2003 | Scroggins | 2/114 |
| 2005/0015127 A1 | 1/2005 | Bieberich | 607/104 |
| 2005/0143796 A1 | 6/2005 | Augustine et al. | 607/104 |
| 2006/0047332 A1 | 3/2006 | Malmberg et al. | 607/104 |
| 2006/0122671 A1 | 6/2006 | Albrecht et al. | 607/104 |
| 2006/0122672 A1 | 6/2006 | Anderson | 607/104 |
| 2006/0147320 A1 | 7/2006 | Hansen et al. | 417/313 |
| 2006/0184216 A1 | 8/2006 | Van Duren | 607/104 |
| 2006/0184217 A1 | 8/2006 | Van Duren | 607/104 |
| 2006/0184218 A1 | 8/2006 | Bieberich | 607/104 |
| 2006/0259104 A1 | 11/2006 | Panser | 607/104 |
| 2007/0093882 A1 | 4/2007 | Anderson et al. | 607/104 |
| 2007/0093883 A1 | 4/2007 | Anderson et al. | 607/104 |
| 2007/0093884 A1 | 4/2007 | Anderson et al. | 607/104 |
| 2007/0093885 A1 | 4/2007 | Anderson et al. | 607/104 |
| 2007/0239239 A1 | 10/2007 | Albrecht et al. | 607/96 |
| 2008/0027521 A1 | 1/2008 | Bieberich | 607/96 |
| 2008/0027522 A1 | 1/2008 | Bieberich | 607/96 |
| 2008/0125840 A1 | 5/2008 | Anderson | 607/96 |
| 2008/0177361 A1 | 7/2008 | Anderson | 607/108 |
| 2009/0062891 A1 | 3/2009 | Bieberich | 607/104 |
| 2009/0149931 A9 | 6/2009 | Anderson | 607/104 |
| 2009/0228083 A1 | 9/2009 | Anderson et al. | 607/107 |

FOREIGN PATENT DOCUMENTS

| | | |
|---|---|---|
| GB | 475811 | 11/1937 |
| GB | 1 462 033 | 1/1997 |
| SE | 525 415 C2 | 2/2005 |
| WO | WO 97/14381 A1 | 4/1997 |
| WO | WO 98/48652 A1 | 11/1998 |
| WO | WO 00/62726 A1 | 10/2000 |
| WO | WO 03/086500 A2 | 10/2003 |
| WO | WO 03/106897 A3 | 12/2003 |
| WO | WO 2004/004500 A1 | 1/2004 |
| WO | WO 2006/020170 A1 | 2/2006 |
| WO | WO 2006/062910 A1 | 6/2006 |
| WO | WO 2006/063027 A1 | 6/2006 |
| WO | WO 2006/086587 A1 | 8/2006 |
| WO | WO 2007/047917 A1 | 4/2007 |
| WO | WO 2008/013603 A1 | 1/2008 |
| WO | WO 2008/091486 A2 | 7/2008 |

OTHER PUBLICATIONS

C.B. Mahony & J. Odom, Maintaining intraoperative normothermia: A meta-analysis of outcomes with costs. *AANA Journal*. Apr. 1999. v. 67, No. 2:155-164.

Porta-Chill—The Portable Air-Chiller—Brochure, http://www.portachil.com/, Dec. 3, 1922.

International Search Report & Written Opinion in PCT/US2005/025355, mailed Dec. 1, 2005.

International Search Report & Written Opinion in PCT/US2005/043968, mailed Apr. 19, 2006.

International Search Report & Written Opinion in PCT/US2005/044214, mailed Apr. 19, 2006.

International Search Report & Written Opinion in PCT/US2006/004644, mailed Dec. 18, 2006.

International Search Report & Written Opinion in PCT/US2006/041028, mailed Feb. 20, 2007.

International Search Report & Written Opinion in PCT/US2007/013073, mailed Nov. 9, 2007.

International Search Report & Written Opinion in PCT/US2008/000141, mailed Nov. 11, 2008.

EPO Examination Report mailed Oct. 24, 2006, in EP03719690.4, EP Regional Phase of PCT/US2003/11128 (published as WO/2003/086500).

EPO Examination Report mailed Dec. 17, 2007, in EP03719690.4, EP Regional Phase of PCT/US2003/11128 (published as WO/2003/086500).

EPO Examination Report mailed Jan. 8, 2008, in EP05853005.6, EP Regional Phase of PCT/US2005/043968 (published as WO/2006/062910).

EPO Examination Report mailed Sep. 2, 2008, in EP05789978.3, EP Regional Phase of PCT/US2005/025355 (published as WO/2006/020170).

EPO Examination Report mailed Jan. 23, 2009, in EP05853202.9, EP Regional Phase of PCT/US2005/044214 (published as WO/2006/063027).

EPO Examination Report mailed Apr. 24, 2009, in EP06826351.6, EP Regional Phase of PCT/US2006/041028 (published as WO/2007/047917).

EPO Examination Report mailed Jun. 22, 2009, in EP05853202.9, EP Regional Phase of PCT/US2005/043968 (published as WO/2006/062910).

Applicants' response to the Examination Report in EP06826351.6, mailed Aug. 20, 2009.

EPO Examination Report mailed Sep. 3, 2009 in EP 07795671.2, EP Regional Phase of PCT/US2007/013073 (published as WO/2008/013603).

EPO Examination Report mailed Sep. 29, 2009, in EP06720577.3, EP Regional Phase of PCT/US2006/004644 (published as WO/2006/086587).

EPO Examination Report mailed Apr. 14, 2010 in EP06826351.6, EP Regional Phase of PCT/US2006/041028 (published as WO/2007/047917).

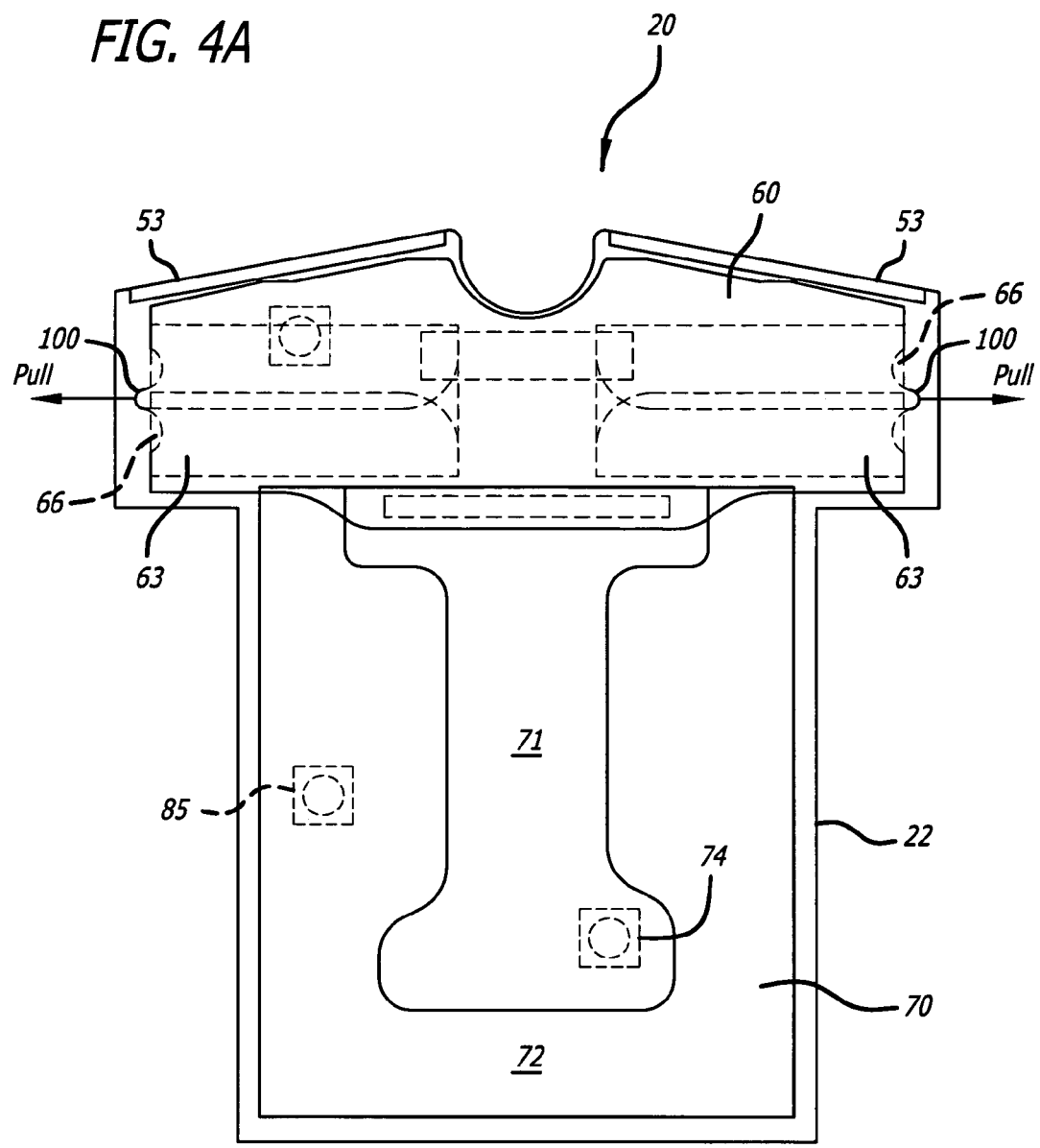

WARMING DEVICE WITH PROVISIONS FOR DEPLOYING ELEMENTS OF AN UPPER BODY CONVECTIVE APPARATUS AND FOR DEPLOYING THE LOWER PORTION OF THE WARMING DEVICE

RELATED APPLICATIONS

This application is a continuation-in-part of U.S. patent application Ser. No. 11/583,432, filed Oct. 19, 2006, entitled "Multifunction Warming Device for Perioperative Use", and is a continuation-in-part of U.S. patent application Ser. No. 11/583,477, filed Oct. 19, 2006, entitled "Multifunction Warming Device with Provision for Being Secured", and is a continuation-in-part of U.S. patent application Ser. No. 11/583,480, filed Oct. 19, 2006, entitled "Multifunction Warming Device with Provision for Warming Hands", and is a continuation-in-part of U.S. patent application Ser. No. 11/583,481, filed Oct. 19, 2006, entitled "Multifunction Warming Device with an Upper Body Convective Apparatus", all of which claim priority under 35 USC §119 to U.S. provisional patent application 60/729,000, filed Oct. 20, 2005, and to U.S. provisional patent application 60/835,602, filed Aug. 4, 2006.

This application contains subject matter related to the subject matter of the following patent applications, all commonly owned herewith:

Patent Cooperation Treaty (PCT) Application No. PCT/US03/011128, filed Apr. 10, 2003, entitled "Patient Comfort Apparatus and System", and published on Oct. 23, 2003 under Publication No. WO 2003/086500;

PCT Application No. PCT/US05/025355, filed Jul. 18, 2005, entitled "Perioperative Warming Device", and published on Feb. 23, 2006 under Publication No. WO 2006/020170;

PCT Application No. PCT/US05/043968, filed Dec. 6, 2005, entitled "Warming Device with Varied Permeability", and published on Jun. 15, 2006 under Publication No. WO 2006/062910;

PCT Application No. PCT/US05/044214, filed Dec. 6, 2005, entitled "Warming Device", and published on Jun. 15, 2006 under Publication No. WO 2006/063027;

PCT Application No. PCT/US06/004644, filed Feb. 9, 2006, entitled "Warming Device for Perioperative Use", and published on Aug. 17, 2006 under Publication No. WO 2006/086587;

PCT Application No. US/2006/041028, filed Oct. 19, 2006, entitled "Multifunction Warming Device for Perioperative Use", and published on Apr. 26, 2007 under Publication No. WO2007/047917;

PCT Application No. PCT/US2007/013073, filed Jun. 1, 2007, entitled "Warming Device", and published on Jan. 31, 2008 under Publication No. WO2008/013603;

PCT Application No. PCT/US2008/000141, filed Jan. 4, 2008, entitled "Convective Warming Device With a Drape", published on Jul. 31, 2008 under Publication No. WO 2008/091486;

U.S. patent application Ser. No. 10/411,865, filed Apr. 10, 2003, entitled "Patient Comfort Apparatus and System" and published on Oct. 16, 2003 under Publication No. US 2003/0195596 and issued on Feb. 21, 2006 under U.S. Pat. No. 7,001,416;

U.S. patent application Ser. No. 10/508,319, 371(c) date Mar. 3, 2005, entitled "Patient Comfort Apparatus and System" and published on Jun. 30, 2005 under Publication No. US 2005/0143796;

U.S. patent application Ser. No. 10/895,672, filed Jul. 21, 2004, entitled "Perioperative Warming Device", now abandoned, published on Jan. 20, 2005, under Publication No. US 2005/0015127;

U.S. patent application Ser. No. 11/005,883, filed Dec. 7, 2004, entitled "Warming Device with Varied Permeability" and published on Jun. 8, 2006 under Publication No. US 2006/0122671, now U.S. Pat. No. 7,226,454;

U.S. patent application Ser. No. 11/006,491, filed Dec. 7, 2004, entitled "Warming Device" and published on Jun. 8, 2006 under Publication No. US 2006/0122672, now U.S. Pat. No. 7,364,584;

U.S. patent application Ser. No. 11/057,396, filed Feb. 11, 2005, entitled "Perioperative Warming Device", and published on Aug. 17, 2006 under Publication No. US 2006/0184215, now U.S. Pat. No. 7,276,076;

U.S. patent application Ser. No. 11/057,397, filed Feb. 11, 2005, entitled "Thermal Blanket for Warming the Limbs", and published on Aug. 17, 2006 under Publication No. US 2006/0184216;

U.S. patent application Ser. No. 11/057,403, filed Feb. 11, 2005, entitled "Warming Device for Perioperative Use", and published on Aug. 17, 2006 under Publication No. US 2006/0184217;

U.S. patent application Ser. No. 11/057,404, filed Feb. 11, 2005, entitled "Clinical Garment for Comfort Warming and Prewarming", and published on Aug. 17, 2006 under Publication No. US 2006/0184218;

U.S. patent application Ser. No. 11/363,136, filed Feb. 27, 2006, entitled "Forced Air Warming Unit" and published on Jul. 6, 2006 under Publication No. US2006/0147320;

U.S. patent application Ser. No. 10/895,672, filed Jul. 21, 2004, entitled "Perioperative Warming Device", now abandoned, published on Jan. 20, 2005, under Publication No. US 2005/0015127;

U.S. patent application Ser. No. 11/057,397, filed Feb. 11, 2005, entitled "Thermal Blanket for Warming the Limbs", and published on Aug. 17, 2006 under Publication No. US 2006/0184216;

U.S. patent application Ser. No. 11/260,706, filed Oct. 27, 2005, entitled "Patient Comfort Apparatus and System", and published on Mar. 9, 2006 under Publication No. US 2006/0052853;

U.S. patent application Ser. No. 11/492,425, filed Jul. 25, 2006, entitled "Warming Device", and published on Nov. 16, 2006 under Publication No. US 2006/0259104;

U.S. patent application Ser. No. 11/656,777, filed Jan. 23, 2007, entitled "Convective Warming Device With a Drape", and published Jul. 24, 2008 under Publication No. US 2008/0177361;

U.S. patent application Ser. No. 11/704,547, filed Feb. 9, 2007, entitled "A Forced Air Warming Unit", and published on Aug. 14, 2008 under Publication No. US 2008/0195184;

U.S. patent application Ser. No. 11/801,292, filed May 9, 2007, entitled "Warming Device with Varied Permeability", and published on Oct. 11, 2007 under Publication No. US 2007/023939;

U.S. patent application Ser. No. 11/899,872, filed Sep. 7, 2007, entitled "Perioperative Warming Method", and published on Jan. 31, 2008 under Publication No. US 2008/0027522;

U.S. patent application Ser. No. 11/899,928, filed Sep. 7, 2007, entitled "Perioperative Warming Device" and published on Jan. 31, 2008 under Publication No. US 2008/0027521; and, U.S. patent application Ser. No. 12/290,713, filed Nov. 3, 2008, entitled "Clinical Garment for Comfort Warming and Prewarming", and published on Mar. 5, 2009 under Publication No. US 2009/0062891.

BACKGROUND

The field relates to a warming device having a clinical garment with at least one convective apparatus supported on an inside surface. More particularly, the field relates to warming device constructions including an upper body convective apparatus with components deployable from the sleeves of a clinical garment and to warming device constructions including a lower, multi-section convective apparatus having a therapeutic section inlet port located midway between the top and bottom edges of the lower multi-section convective apparatus.

In this specification, use of the term "convective" to denote the transfer of heat from a device to a body refers to the device's principal mode of heat transfer, it being understood that heat may at the same time be transferred from the device to the body by conduction and radiation, although not to the degree of convection.

Related art pertinent to convective devices that transfer heat to a human body is known. These devices are typically called "convective thermal blankets", "covers", "warming blankets", or "thermal blankets". Arizant Healthcare Inc., the assignee of this application, makes and sells such devices under the BAIR HUGGER® brand. One such device is the Model 522 Upper Body Blanket.

Thermal blankets are designed for particular deployments where therapeutic warming is indicated. Three representative thermal blankets known in the prior art are shown in FIGS. 1A-1D. A "full body" thermal blanket 10 is shown in FIG. 1A. The full body thermal blanket is adapted to lie upon a person and to extend longitudinally along the body of the person in order to cover substantially the person's entire body, from near the ankles or feet up to the neck. A "lower body" thermal blanket 12 is shown in FIG. 1B. The lower body thermal blanket 12 is adapted to lie upon the person and to extend longitudinally along the body of a person in order to cover the person's lower body, from near the ankles or feet up to the waist or pelvis of the person. Either (or both) of the thermal blankets 10, 12 may include a drape at one or more of its side and lower edges to trap and retain warmed air expelled through the blanket about the limbs of a person to aid in therapeutic warming during surgery. For example, the lower body thermal blanket 12 includes a foot drape 13 at its lower edge.

An "upper body" thermal blanket 15 is illustrated in FIGS. 1C and 1D. The upper body thermal blanket 15 has a bow-tie shape that is adapted to lie upon and extend transversely across the upper body of a person in order to cover the person's chest and extended arms. A head drape 16 may be formed on or attached to the upper body thermal blanket 15 for draping over the head 17 of a person in order to retain warmed air expelled through the blanket 15 about the head to aid in therapeutic warming during surgery.

When fed a stream of warmed pressurized air, each of the thermal blankets 10, 12, 15 inflates and distributes the air within itself. While the thermal blanket lies on the person, the warmed pressurized air flows through apertures or interstices in a permeable surface of the thermal blanket which faces the person. These thermal blankets may have one, two, or more inlet ports 18 through which an air hose 19 provides warmed pressurized air from a heater/blower unit (not shown in these drawings).

Related art pertinent to thermal blankets includes specific constructions described in U.S. Pat. No. 5,620,482, U.S. Pat. No. 5,443,488, U.S. Pat. No. 5,360,439, and U.S. Pat. No. 5,304,213. See also U.S. Pat. No. 5,974,605.

Related art pertinent to a warming device includes adaptation of a clinical garment such as a robe or gown to receive a convective device in order to warm a person wearing the garment in a clinical setting for comfort and mobility of the person is disclosed in the referenced Publication No. WO 2003/086500.

The term "perioperative" is defined in the PDR Medical Dictionary, Second Edition, (Medical Economics Company, 2000), as "around the time of operation." The perioperative period is characterized by a sequence including the time preceding an operation when a patient is being prepared for surgery ("The preoperative period"), followed by the time spent in surgery ("the intraoperative period"), and by the time following an operation when the patient is closely monitored for complications while recovering from the effects of anesthesia ("the postoperative period").

Related art pertinent to warming device constructions which may be used perioperatively includes a clinical garment such as a robe or gown that receives one or more convective devices in order to warm a person for comfort or therapy is disclosed in US publications 2007/0093882 A1; 2007/0093883 A1; 2007/0093884 A1; and, 2007/0093885 A1.

The applicants know of previously proposed warming device constructions which include an upper body convective apparatus supported on an inside surface of a clinical garment with deployable elements of the upper body convective apparatus folded in the sleeves of the clinical garment. The folded elements are retained between the clinical garment and the upper body device, with folded ends tucked into cuffs formed on inside surfaces at the ends of the sleeves. To deploy the elements, the ends of the sleeves are opened and the folded ends of the upper body device are pulled from the cuffs. The mechanisms used to open the sleeves require complicated steps in the warming device manufacturing process, which adds to the cost and time of manufacture.

The applicants also know of previously proposed warming device constructions which include a lower convective apparatus supported on an inside surface of a clinical garment and a drape deployed past the lower hem of the clinical garment to trap and retain heated air about the lower limbs and feet. The drape is furled and positioned near the lower hem, and is deployed from that location over the lower portion and feet of the body which is warmed by operation of a therapeutic warming section of the lower convective apparatus. The drape requires complicated steps in the warming device manufacturing process, which adds to the cost and time of manufacture.

SUMMARY

In some aspects, warming device constructions include a clinical garment with at least one convective apparatus supported on the inside of the garment. In some aspects, the convective apparatus includes an upper body convective apparatus extending between the sleeves of the clinical garment. Pulling elements that draw folded components of the upper body convective apparatus from sleeves of the clinical garment when pulled are provided on the lateral extensions of the apparatus to unfold the extensions from the sleeves. Some constructions may include a lower, multi-section convective apparatus supported on the inside surface, beneath the sleeves. In some aspects, a therapeutic section inlet port is provided in a location midway between the top and bottom edges of the lower, multi-section convective apparatus where the therapeutic section inlet port will be supported above a person's lower extremities when the lower portion of the warming device is used to therapeutically warm the lower extremities of a person.

BRIEF DESCRIPTION OF THE DRAWINGS

FIG. 4A is a plan view showing the warming device with ends of the upper body convective apparatus folded into the sleeves of the clinical garment and a pulling element associated with the folded ends.

DETAILED DESCRIPTION OF PREFERRED EMBODIMENTS

A warming device is constituted of a clinical garment and at least one convective apparatus supported on an inside surface of the garment. In this regard, a "clinical garment" is a garment used to temporarily clothe a patient in a clinical setting. Such garments include hospital gowns, robes, bibs and other equivalents. The clinical setting may be a medical or dental office or clinic, a hospital, or any facility or institution that provides medical or dental treatment to patients. A convective apparatus receives and distributes at least one stream of warmed pressurized air in a structure for being disposed on, adjacent, or next to the core and/or the limbs of a body. When pressurized with warmed air, a convective apparatus emits warmed air through one or more of its surfaces.

Of course, although the device is herein referred to as a "warming" device and is described as operating with warmed, pressurized air, it may also operate with pressurized air at ambient temperature or cooled, pressurized air. Moreover, it may be useful to operate the device with pressurized air that includes a mixture of selected constituents including water vapor, medicaments, scented compounds, and so on.

In one aspect, a warming device may be worn on a person where it receives a stream of warmed pressurized air, distributes the pressurized air within a convective apparatus, and emits the air through one or more surfaces of the convective apparatus to warm the person's body.

In the warming device illustrated and described below, the convective apparatuses are inflatable. That is, their structures, flaccid when not in use, tauten when receiving a stream of pressurized air.

Exemplary warming device constructions include a clinical garment supporting at least one, and preferably two convective apparatuses on an inside surface. In some aspects, an elongated, upper body convective apparatus supported on the inside surface in the upper portion of the clinical garment, extends between the sleeves. In some aspects, a lower, multi-section convective apparatus is supported on the inside surface, beneath the upper portion. In yet other aspects, both upper body and lower multi-section convective apparatuses are supported on the inside surface, from the upper portion to the lower hem.

Figure 1A:
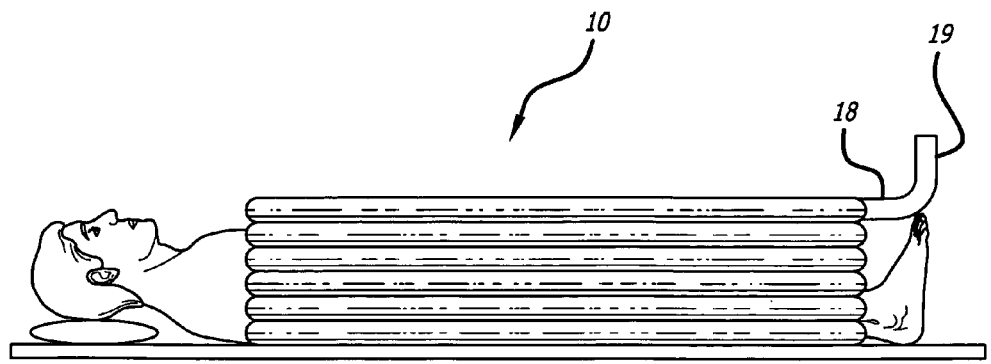
FIGS. 1A-1D are illustrations of prior art full body, lower body, and upper body convective thermal blankets.
Figure 1B:
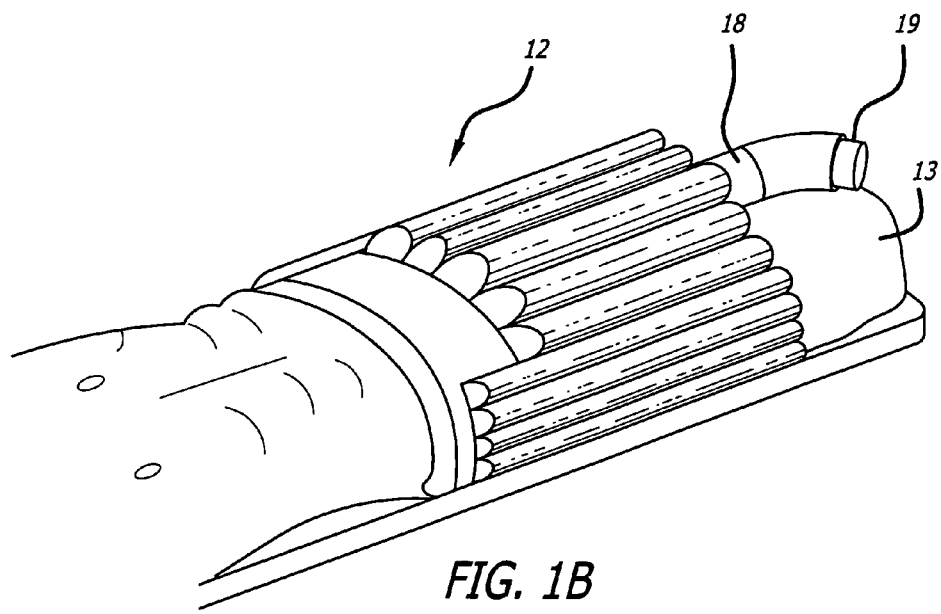
Figure 1C:
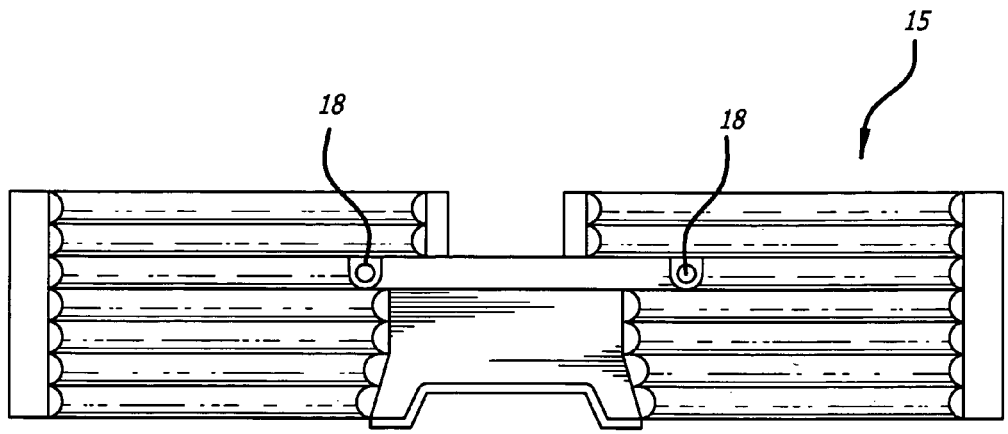
Figure 1D:
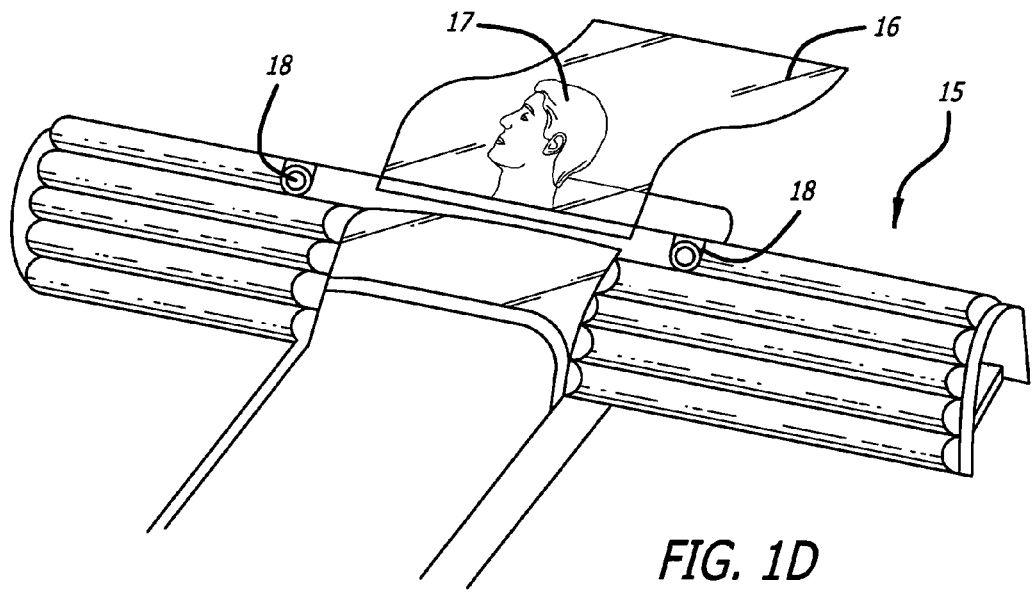
Figure 2:
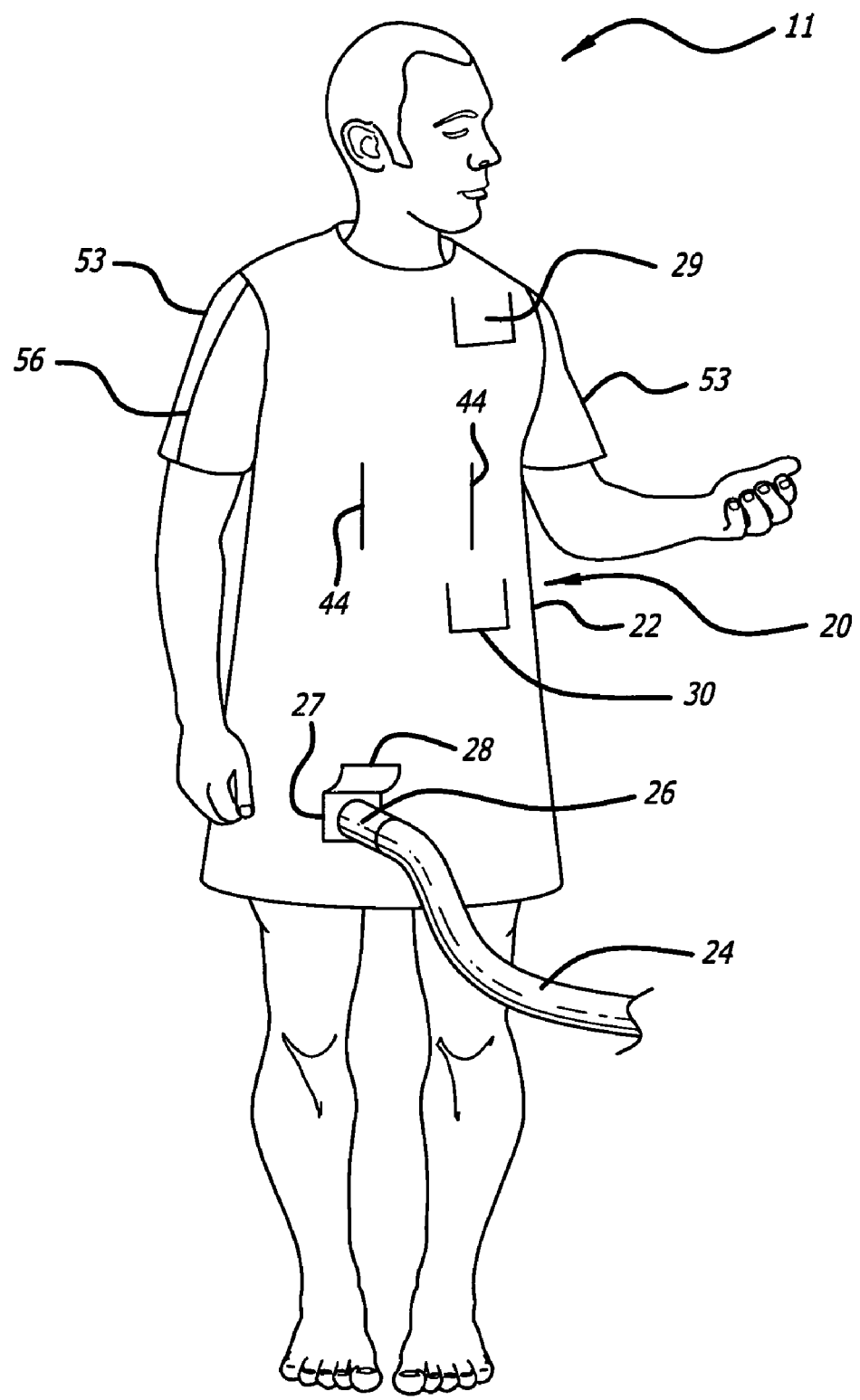
FIG. 2 is an illustration of a person wearing a warming device having a clinical garment and a convective warming device supported inside the clinical garment.

Refer now to FIG. 2, a person wearing a warming device 20 is illustrated. The warming device 20 is constituted of a clinical garment 22 and at least one convective apparatus (not seen in this view) supported on an inside surface of the clinical garment 22. A convective apparatus supported on the inside surface of the clinical garment 22 is operated by receiving warmed, pressurized air from a heater/blower unit (not seen in this view) through an air hose with a nozzle that is received in an inlet port of the convective apparatus. One such air hose 24, with a nozzle 26, is shown in FIG. 2. One such inlet port is indicated by reference numeral 27 in FIG. 2. The inlet port 27 is accessed through a flap 28 covering an opening in the clinical garment 22. Other openings to other inlet ports may be accessed through other flaps, such as flaps 29 and 30.

Figure 3A:
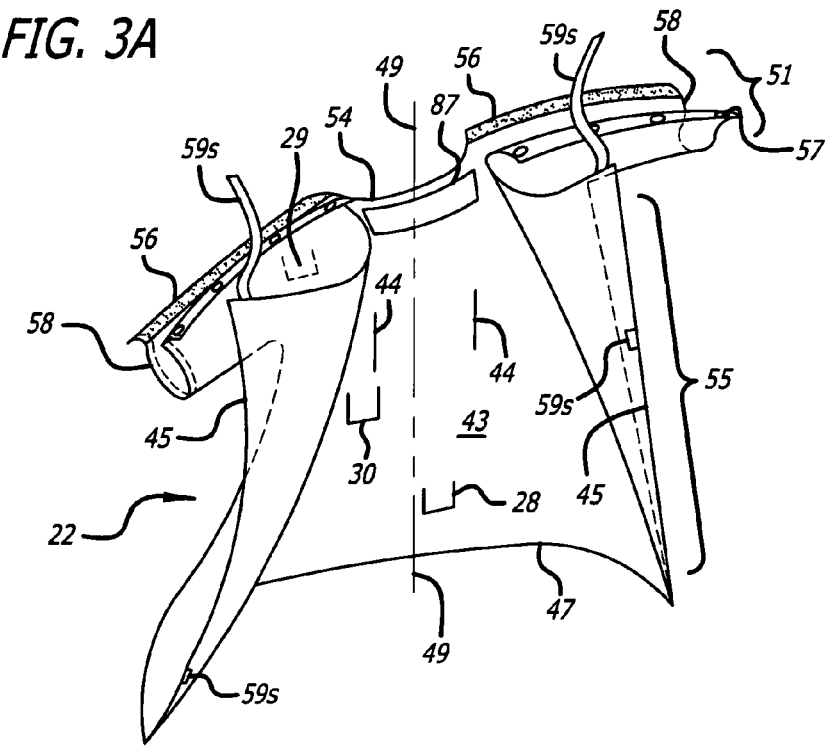
FIG. 3A is a perspective view of the clinical garment showing an inside surface to support one or more convective apparatuses.
Figure 3H:
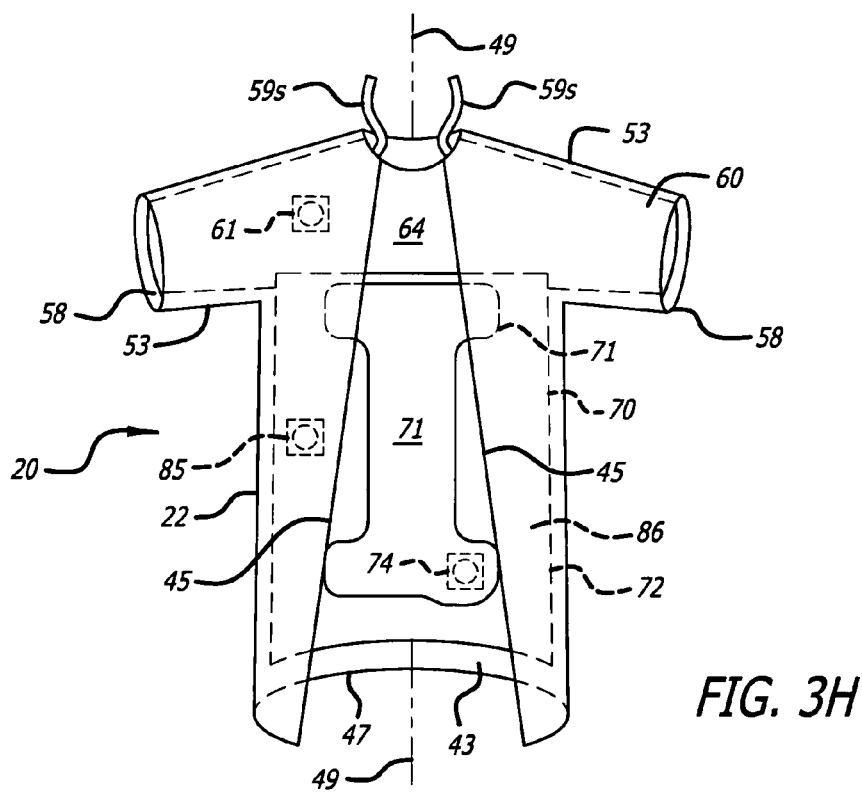
FIG. 3H is a rear elevation view of a warming device.
Figure 3B:
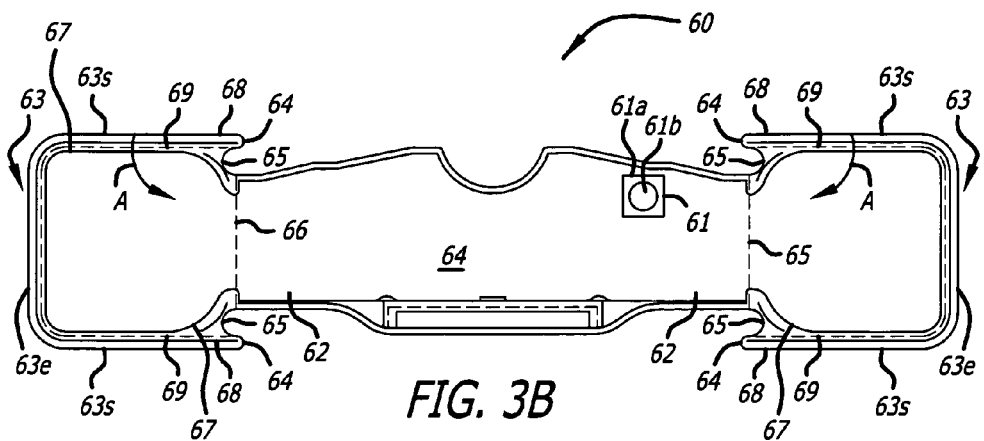
FIGS. 3B, 3C and 3D are plan views of an upper body convective apparatus showing the structure of the apparatus unfolded, partially folded, and finally folded, respectively.
Figure 3C:
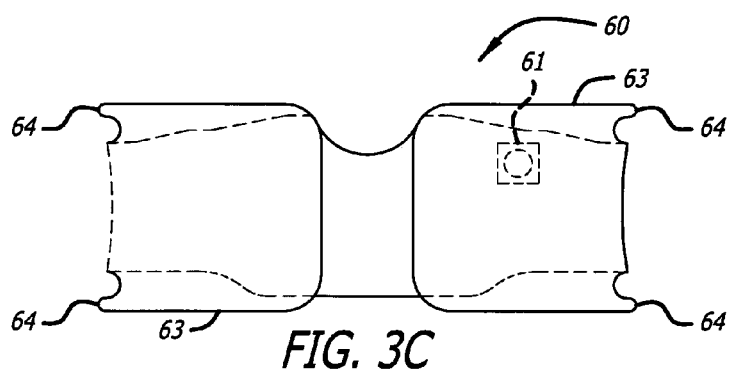
Figure 3D:
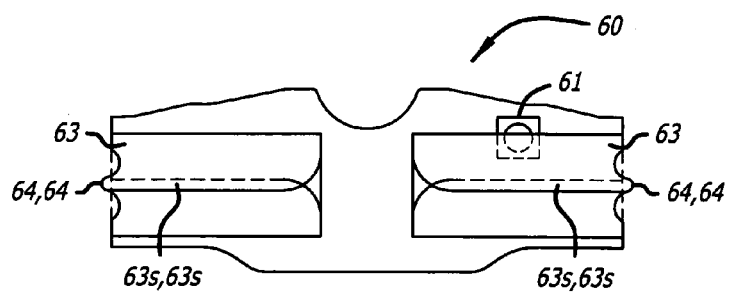
Figure 3E:
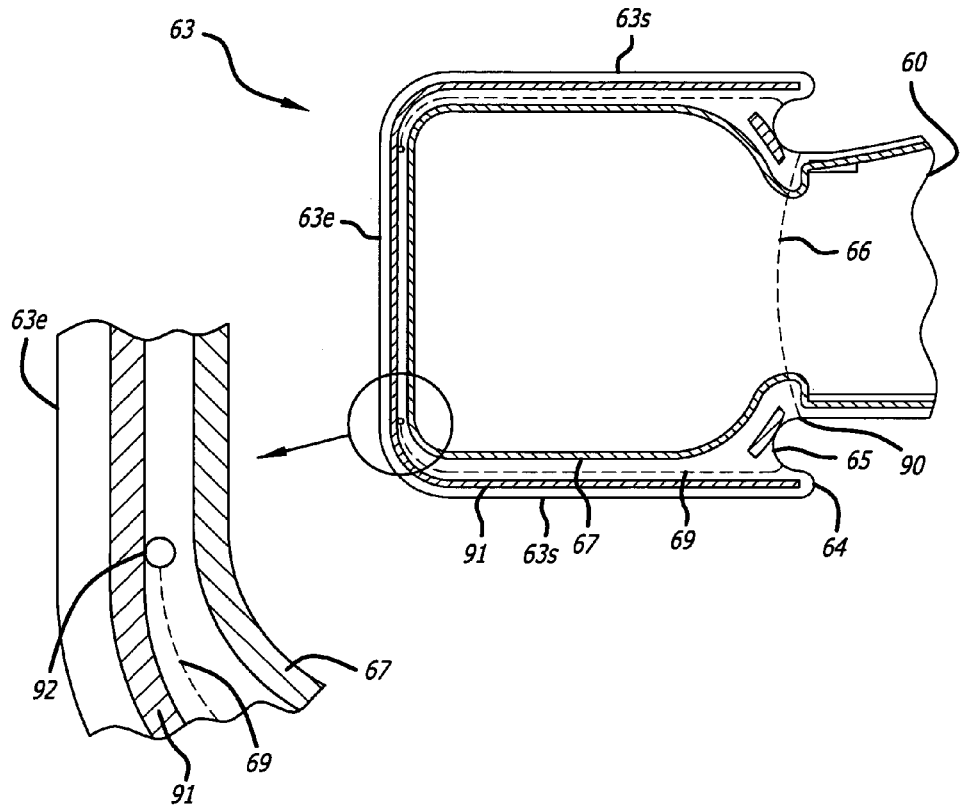
FIG. 3E is an enlarged view of an end portion of the upper body convective apparatus, with a magnified view showing details thereof.
Figure 3G:
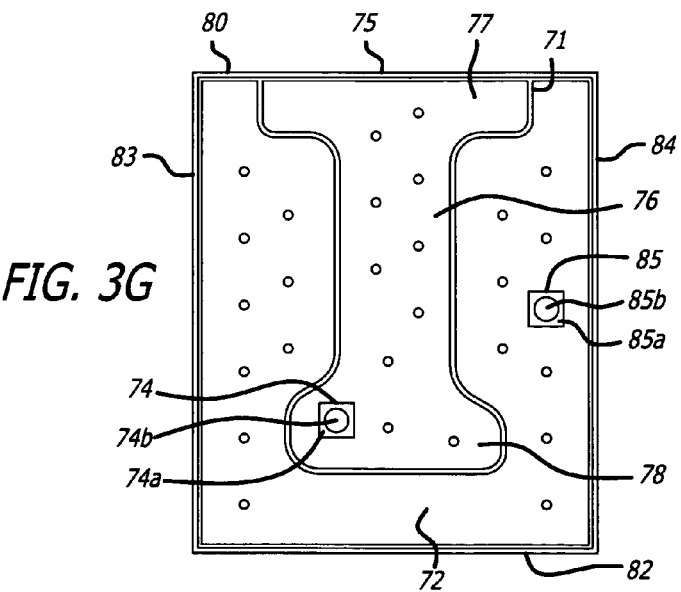
FIG. 3G is a plan view of a multi-section convective apparatus.

FIGS. 3A through 3F illustrate elements of a warming device; the assembled warming device 20 is itself illustrated in FIG. 3G. The view in FIGS. 3A and 3G is from the rear of the clinical garment 22, looking toward the inside surface of the garment, which faces the chest, or thorax of a patient and on which at least one convective apparatus is supported. FIGS. 3B through 3F are plan views of un-inflated convective apparatuses, looking toward an impermeable surface of each apparatus. As seen in FIGS. 2, 3A and 3G, the warming device 20 includes the clinical garment 22. The clinical garment 22 includes an inside surface 43, two opposing lateral hems 45, a lower hem 47, and a longitudinal axis 49. The clinical garment 22 has an upper portion 51 with two opposing sleeves 53 and a scooped upper edge 54, and a lower portion 55. The clinical garment may have two slits 44. The flaps 28, 29, and 30 that provide access to inlet ports through the front of the garment 22 are also visible in FIG. 3A. The sleeves 53 may be long or short. Short sleeves are preferred if access must be had to a person's arms for instrumentation and/or IV delivery. Each sleeve 53 may have an elongate seam 56. Each seam 56 may be held closed by means 57 including, for example, buttons, snaps, hook and loop material, tape, and/or straps, or any equivalent thereof. Such means can be operated to let a seam 56 be opened and to again close a seam, once opened. The clinical garment 22 may open on a side. Preferably, the clinical garment 22 opens in the rear. The opening may be full, as illustrated in FIG. 3A, or it may be a slit rising from above the lower hem 47. As per the example shown in FIG. 3A, the opening may be closed by means along the lateral hems 45 which releasably connect to keep the hems together. Such means may include, for example, buttons, snaps, hook and loop material, tape, and/or straps, or any equivalent thereof. For example, integrally-formed straps 59s for tying the opposing lateral hems 45 together in the upper portion 51 are seen in FIG. 3A. The clinical garment 22 may be constructed from non-woven or woven materials. Preferably, the clinical garment 22 is made from a non-woven blend of polyester with a natural fiber such as wood pulp.

In FIG. 3B, an upper body convective apparatus 60 to provide therapeutic warming is shown fully opened. In FIG. 3C, elements of the upper body convective apparatus 60 are shown partially folded; FIG. 3D shows the elements fully folded. The view in these figures is toward an impermeable surface of the upper body convective apparatus 60 which faces the inside surface of the clinical garment. As seen in these figures, the upper body convective apparatus 60 includes an inlet port 61, two lateral extensions 62, each transitioning to a respective end 63, an impermeable surface 64, and a lower edge E. An air permeable surface is on the side of the upper body convective apparatus not visible in these figures.

As seen in FIG. 3B, each end 63 has a generally quadrilateral configuration with a periphery including opposing, parallel side edges 63s and an outside end edge 63e. Each side edge 63s is terminated at one end by a tab 64 which points away from the end edge 63e, toward the center portion of the upper body convective apparatus 60, when the apparatus is unfolded. From a tab 64, the periphery of an end 63 transitions through an indentation 65 to a transverse line of weakness 66 where the end 63 joins the central portion of the upper body convective apparatus 60. The transverse line of weakness 66 may be constituted of a trace or pattern of perforations extending transversely across the apparatus 60 from one indentation 65 to the other. Typically, the periphery of an end 63 includes a portion of an impermeable seal 67 that follows the entire periphery of the upper body convective apparatus 60. A tie strip 68 is integrally formed or defined in a side periphery of an edge 63 by a peripheral line of weakness 69 that extends from a tab 64, along a side edge 63s in which the tab is formed. Each peripheral line of weakness 69 may be constituted of a trace or pattern of perforations extending along the periphery at a side of an end 63. Preferably, the tie strips 68 are used to secure the upper body convective apparatus 60 during use. For example the tie strips may secure the apparatus to the cruciate member of a surgical table on which a person's outstretched arms are supported. See the assignee's U.S. Pat. No. 5,773,275 in this regard.

With reference to FIG. 3E, when a tab 64 is grasped and pulled away from an indentation 65, the tie strip 68 associated with the tab begins to separate from an end 63. In separating a tie strip 68 in this way, it is desirable to cantilever the tab 64 over an indentation 65 because the separating force applied on the tab 64 is directed along the associated peripheral line of weakness 69, instead of downwardly into the end 63. A truncated seal or stake point 90 may be provided adjacent the indentation 65 to guide the separating force to the peripheral line of weakness 69.

It is further desirable to reduce tendencies for the separating force to be diverted toward a side edge or across an end edge, either of which can result in a tie strip being torn altogether from an end. Certain constructions which keep the separating force confined to the track of a line of weakness can prevent such occurrences. Referring again to FIG. 3E, in some aspects of warming device construction, peripheral lines of weakness 69 may be formed in each end 63 between the impermeable seal 67 and a peripheral seal 91 running just inside the periphery of the end 63. This will tend to confine a tearing force along a peripheral line of weakness 69 to a track between the seals 67 and 91. Further, to prevent the separating force from ripping through the end of a side edge 63s, the track and the peripheral line of weakness 69 may be curved where the side edge 63s transitions to an end edge 63e. Thus, at the end edge 63e, each peripheral line of weakness 69 turns from a side edge 63s to extend at least partially along the end edge 63e. It may also be effective to terminate each line of weakness 69 in a hole through the track. For example, such a hole 92 may be located in the end edge 63e when the peripheral line of weakness 69 curves into the end edge 63e.

Figure 3F:
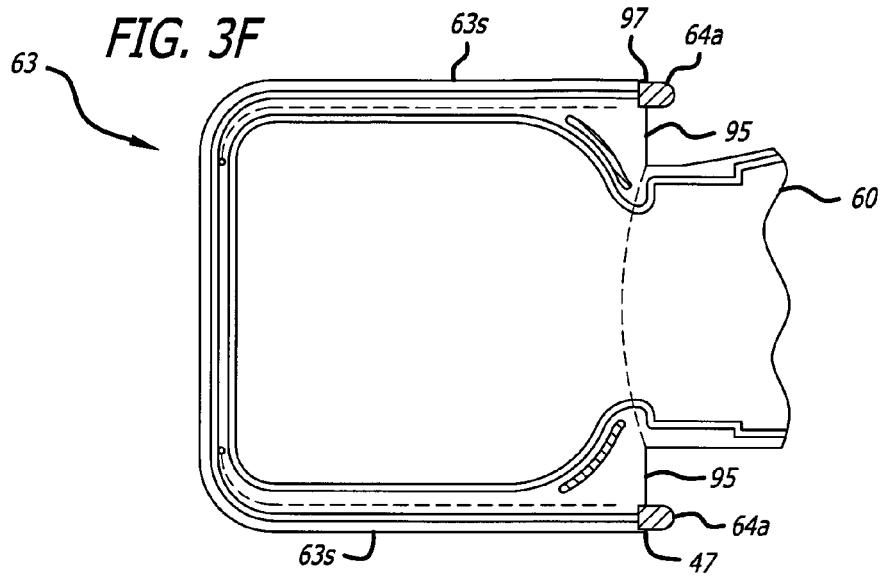
FIG. 3F is a enlarged view of an alternate embodiment of the end portion of the upper body convective apparatus.

In an alternate embodiment, seen in FIG. 3F, the side edges 63s transition to the center portion of the upper body convective apparatus 60 along straight edges 95 instead of indentations. The tabs 64a are extensions of the side edges that face the center portion at the corners 97 where the edges 63s and 95 meet. The tabs 64a are preferably of the same materials as the upper body convective apparatus and may be formed integrally with the side edges 63s by cutting or stamping, or may be formed separately and applied by gluing, heat sealing, stapling, or welding to the corners 97.

As seen in FIG. 3B, in order to stow the upper body convective apparatus 60 prior to use, the corresponding sides of the ends 63 are folded toward each other at creases along the transverse lines of weakness 66, as indicated by the arrows A, over the impermeable surface 64 as per FIG. 3C. The opposing side edges 63s of the ends are then folded together so as to overlap and align the tabs 64 as shown in FIG. 3D. The folds reduce each lateral extension 62 to a length that fits in a respective sleeve 53 of the clinical garment 22. The folds are preferably made so as to be retained between the clinical garment 22 and the upper body convective apparatus 60. This allows the user to insert an arm through the sleeve of the clinical garment 22 without engaging a fold and inadvertently deploying the associated folded end.

Figure 4B:
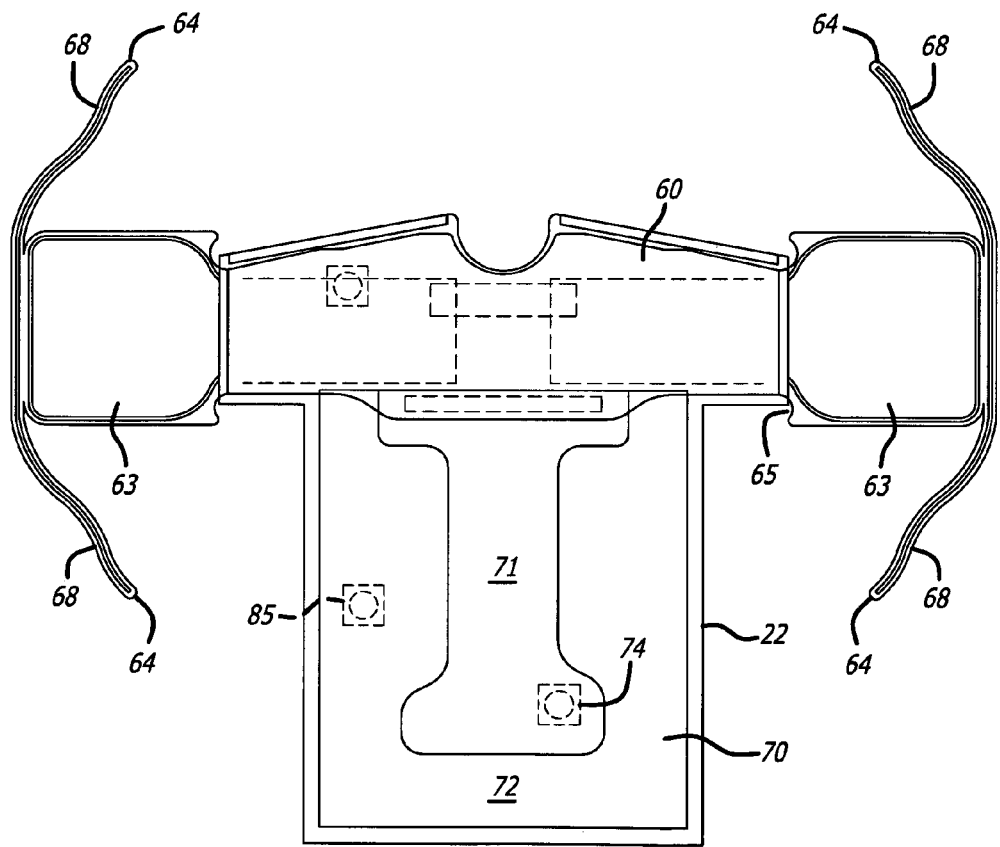
FIG. 4B is a plan view showing the warming device with the ends of the upper body convective apparatus unfolded from the sleeves and tie straps separated from sides of the ends.

When folded as described, the upper body convective apparatus 60 is stowed in the warming device 20 as shown in FIG. 4A. The ends 63 are folded on creases near the transverse lines of weakness and retained between the impermeable surface of the upper body convective apparatus 60 and the inside surface in the sleeves 53. The overlapping tabs 64 on each end 63 now point away from the end 63 and constitute a pulling element 100 for unfolding the folded end 63 and separating the tie strips 68 from the side edges 63s of the end 63. That is to say, as the pulling elements 100 are pulled from the sleeves 53, the pulling force dislodges and moves the ends from their folded configurations in the sleeves 53. At the same time, the pulling force opens the peripheral lines of weakness 69, thereby separating the tie strips 68 from the side edges 63s of the ends 63. Thus, as seen in FIG. 4B, when the ends 63 are unfolded, the tie strips 68 are also separated from the side edges 63s, but, because of the transitions from side to end edges, are not torn from the ends 63.

The transverse lines of weakness 66 permit separation of the ends 63 after the upper body convective apparatus 60 has been deployed and its use is no longer indicated. Instead of refolding and stowing the lateral extensions 62 of the upper body convective apparatus 60 back into the sleeves 53, the ends 63 can be conveniently removed and discarded. In order to extend the lifetime of machinery used to manufacture the upper body convective apparatus, it is desirable that the transverse lines of weakness 66 not be perpendicular to the longitudinal axis of the upper body convective apparatus 60. In certain manufacturing configurations, a perpendicular transverse line of weakness is formed by cutting a straight line of perforations against an elongate tool in a single stroke. This brings maximum force to bear along the entire cutting edge of the tool. In a high-speed manufacturing line, continuous pounding with maximum force shortens lifetime of the tool. Thus, it may be preferable that the transverse lines of weakness 66 not be perpendicular. Instead, they may be oblique to the longitudinal axis of the upper body convective apparatus 60. Or, the transverse lines of weakness may be non-linear.

For example, the transverse lines of weakness may be triangular. Preferably, as seen in FIG. 3E, the transverse lines of weakness 66 are curved.

In some aspects, the warming device constructions described and illustrated herein may include attachment mechanisms, such as a double-sided tape, and/or head drapes as described in US publications 2007/0093882 A1; 2007/0093883 A1; 2007/0093884 A1; and, 2007/0093885 A1.

With reference to FIGS. 3B-3D, although one inlet port 61 is illustrated in the upper body convective apparatus 60, one or more additional inlet ports may be provided for convenience. Unused inlet ports are sealed or closed by known means to prevent air escaping therethrough. Preferably the inlet port 61 is provided through the impermeable surface of the upper body convective apparatus 60; it may also be provided through an edge of the upper body convective apparatus 60. The inlet port 61 may comprise a collar 61a of stiff material mounted on the impermeable surface 64 with an opening 61b through the impermeable surface to receive the nozzle of an air hose, or it may comprise a sleeve of material, or any other equivalent structure. When the upper body convective apparatus 60 is used for therapeutic warming, the ends of the apparatus are unfolded from the sleeves 53. Then, pressurized air flowing through an inlet port such as the inlet port 61 inflates the upper body convective apparatus 60, from its central portion to its ends 63.

A multi-section convective apparatus 70 with separately inflatable sections is illustrated in FIG. 3G. Because this convective apparatus is disposed on the inside surface in the lower portion of the clinical garment, it may also be referred to as the "lower convective apparatus" 70. A "section" of the lower convective apparatus 70 is a portion or division that may be inflated and operated separately from any other section. For example, the lower convective apparatus 70 has a comfort section 71 and a therapeutic section 72. The comfort section 71 may be inflated and operated separately from the therapeutic section 72, and the therapeutic section 72 may be inflated and operated separately from the comfort section 71.

In the lower convective apparatus 70 shown in FIG. 3G, the comfort section 71 has an inlet port 74, an upper edge 75, an elongate central part 76, and upper and lower transverse parts 77 and 78 that connect perpendicularly to the central part 76. The ends of the upper and lower transverse parts 77 and 78 may be rounded, so that, in the plan view of FIG. 3G, the comfort section 71 has a "dog bone" shape. Alternatively, the comfort section 71 may have the shape of a capital 1, with upper and lower cross bars. Although one inlet port 74 is illustrated in the comfort section 71, one or more additional inlet ports may be provided for convenience. Unused inlet ports are sealed or closed by known means to prevent air escaping therethrough. Preferably the inlet port 74 is provided through the impermeable surface 88 of the lower convective apparatus 70 which is visible in this figure. The inlet port 74 may comprise a collar 74a of stiff material mounted on a portion of the impermeable surface 88 in the section with an opening 74b opening through the surface to receive the nozzle of an air hose, or it may comprise a sleeve of material, or any other equivalent structure. The space in the central part 76 is in fluid communication with the spaces in the transverse parts 77 and 78 so that pressurized air flowing through the inlet port 74 flows throughout the parts 76-78, thereby inflating the first section 71. The surface of the comfort section 71 which is not visible in FIG. 3G, including the surfaces of the parts 76-78, is permeable, permitting pressurized air that is flowing into and inflating the section 71 to be expelled toward the interior of the clinical garment 22 (that is, toward a patient wearing the device 20). In some aspects of the comfort section 71, the permeability of the permeable surfaces of the parts 76-78 may vary in order to reduce or eliminate variances in temperature of air expelled through the permeable surface of the section.

As seen in FIG. 3G, the therapeutic section 72 has a U-shaped outline with lower edge 82 and side edges 83 and 84. The therapeutic section 72 generally forms an outline that surrounds the comfort section 71 on three sides. Although one inlet port 85 is illustrated in the therapeutic section 72, one or more additional inlet ports may be provided for convenience. Unused inlet ports are sealed or closed by known means to prevent air escaping therethrough. Preferably the inlet port 85 is provided through the impermeable surface 88 of the therapeutic convective apparatus 70 which is visible in FIG. 3G, although it may also be provided through an edge of the lower convective apparatus 70. The inlet port 85 may comprise a collar 85a of stiff material on the impermeable surface 88 with an opening 85b through the impermeable surface to receive the nozzle of an air hose, or it may comprise a sleeve of material, or any other equivalent structure. Pressurized air flowing through the inlet port 85 inflates the therapeutic section 72. The surface of the therapeutic section 72 which is not visible in FIG. 3G is permeable, permitting pressurized air that is flowing into and inflating the therapeutic section 72 to be expelled toward the interior of the clinical garment 22 (that is, toward a patient wearing the device 20).

In some aspects of the lower convective apparatus 70, the upper edge 75 of the first section 71 is part of the upper edge 80 of the lower convective apparatus 70 in order to position the upper transverse part 77 approximately against and transverse to the upper chest, between the shoulders, of a patient wearing the clinical garment 22. This advantageously locates the upper transverse part 77 for delivery of air for comfort warming the chest of the patient.

The dog-bone and U construction of the lower convective apparatus 70 is not intended to be limiting; it is just one example of how the apparatus may be provided with separately-inflatable sections for comfort and therapeutic warming, and other possible two-section constructions are shown and described in related applications that are listed above.

With reference to FIG. 3G, in some aspects of the lower convective apparatus the inlet port 74 of the comfort section 71 may have a smaller opening 74b than the opening 85b through the inlet port 85 of the therapeutic section 72. In this case, the openings 61b of the upper body convective apparatus 60 and 85b of the therapeutic section 72 are preferably of equal size. Consequently, the inlet port 74 accepts an air hose nozzle with a smaller diameter than the air hose nozzle diameter accepted by the inlet ports 61 and 85. The smaller nozzle diameter signifies a comfort warming air supply with an air hose having a smaller diameter than the air hose of a therapeutic warming air supply. Further, the smaller air hose may be coupled to a heater blower unit with a smaller capacity than that of the heater blower unit of a therapeutic warming air supply, which can be connected to either the upper body convective apparatus 60 or the therapeutic section 72 of the lower convective apparatus 70. The provision of an inlet port 74 dimensioned for a smaller-diameter hose enables the comfort section 71 to operate in response to a lower capacity heater/blower unit designed for comfort warming. The provision of inlet ports 61 and 85 dimensioned for a larger-diameter hose enables the upper body convective apparatus 60 and the therapeutic section 72 of the lower convective apparatus 70 to operate in response to a higher capacity heater/blower unit designed for therapeutic warming. The upper apparatus 60 is therefore constructed for therapeutic warming, and the lower convective apparatus 70 has a comfort section 71 constructed for comfort warming and a therapeutic section 72 constructed for therapeutic warming.

As is evident with reference to FIGS. 3G and 3H, the lower convective apparatus 70 is disposed longitudinally to the clinical garment and includes an upper edge 80 near the upper section of the clinical garment, where the upper body convective apparatus is disposed. The lower edge of the lower convective apparatus 70 is near the lower hem 47 of the clinical garment 22. The therapeutic section inlet port 85 is disposed in a middle portion of the lower convective apparatus 70, near a side. Preferably, the therapeutic section inlet port 85 is located substantially midway between the upper edge 80 and the lower edge 82, near one of the side edges, such as the side edge 84. In FIG. 2, the opening covered by the flap 30 through which the therapeutic section inlet port 85 is accessed is formed substantially in a middle portion of the clinical garment 22 so as to be aligned with the therapeutic section inlet port 85 when the lower convective apparatus 70 is supported on the inside surface 43 of the clinical garment 22.

Figure 5:
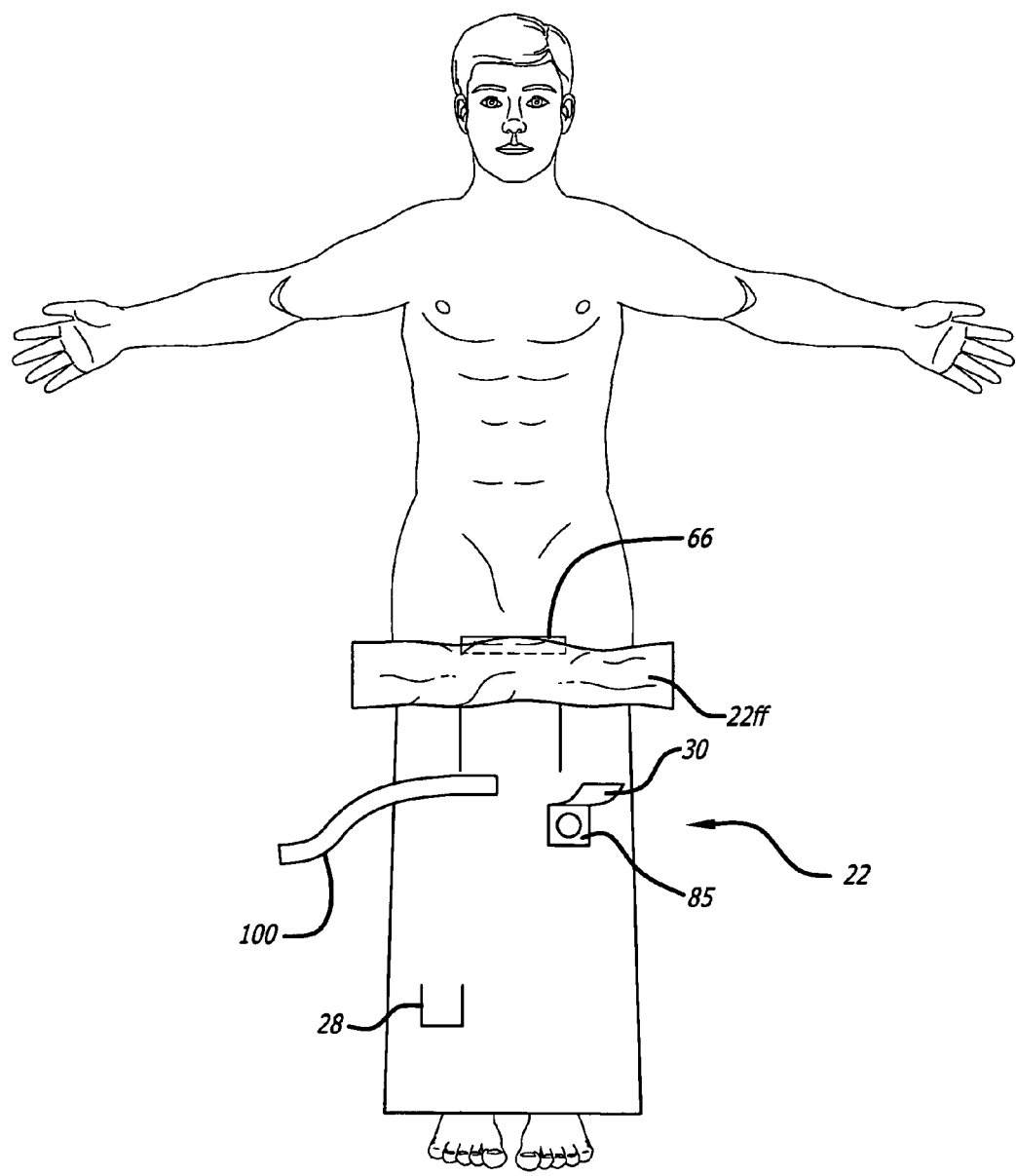
FIG. 5 illustrates deployment of a warming device to therapeutically warm the lower body of a patient.

It is desirable for the therapeutic section inlet port 85 to be positioned substantially midway between the upper and lower edges 80 and 82 of the lower convective apparatus 70. The benefits of deploying a drape past the lower hem of a warming device to cover lower limbs and feet of a person while operating the therapeutic section of a multi-section convective apparatus are described in US publication 2008/0177361. However, in some cases it may be desirable to reduce the complexity and cost of manufacturing a warming device by eliminating the drape, while still realizing the benefits of lower limb draping when warming with the therapeutic section. As is shown in FIG. 5, the person's arms have been removed from the sleeves 53 of the clinical garment 22, the upper section has been partially rolled or folded, and the warming device 20 has been repositioned so as to cover the lower limbs and feet of the person. The therapeutic section inlet port 85 is now positioned over the upper thighs, while the lower part of the warming device 20 covers the lower legs and feet of the person. If the therapeutic section 72 is used, the nozzle and air hose coupled to it are kept out of potential harmful contact with the feet and lower legs by the location of the therapeutic section inlet port 85.

FIG. 3H illustrates the warming device in which both of the convective apparatuses 60 and 70 are supported on the inside surface of the clinical garment 22. However, it is also desirable that warming devices having either, but not both, of the convective apparatuses supported on the inside surface of the clinical garment be provided for particular needs. In any case, as FIG. 3H shows, the upper body convective apparatus 60 is preferably disposed in the upper portion of the clinical garment 22, which includes the sleeves, and the lower convective apparatus 70 is preferably disposed in the lower portion of the clinical garment 22, beneath the upper portion.

FIG. 3H also illustrates a preferred relationship between the convective apparatuses 60 and 70 when both are supported on the inside surface 43 of the clinical garment 22. In this relationship, the upper edge 80 of the lower convective apparatus 70 overlaps the lower edge E of the upper body convective apparatus 60. The upper edge 80 may be retained in place by tacking, taping, or a light adhesive acting between the upper edge 80 and the upper body convective apparatus 60 and/or the inside surface 43 of the clinical garment.

FIG. 3H shows a warming device 20 for perioperative use assembled from the elements illustrated in FIGS. 3A-3D. In the warming device 20, the convective apparatuses 60 and 70 are supported on the inside surface 43 of the clinical garment 22. In FIG. 3H, the view is toward the permeable surfaces of the convective apparatuses 60 and 70. Together the convective apparatuses 60 and 70 form a Tee-shaped figure substantially centered on the longitudinal axis 49, and with a thick base (the lower convective apparatus 70) and an elongate top (the upper body convective apparatus 60) which is perpendicular to the base.

As illustrated in FIG. 3H, the upper body convective apparatus 60 is an elongate convective apparatus disposed, supported, or constructed on the inside surface 43 of the clinical garment 22, in the upper portion 51, transverse to the longitudinal axis 49 and extending from sleeve 53 to sleeve 53. Preferably, the upper body convective apparatus 60 is an upper body convective apparatus having the construction illustrated in FIGS. 3B and 3C, with its ends 63 folded and retained in the sleeves 53. An opening in the upper portion 51 of the clinical garment 22 (such as the flap 29 in FIGS. 2 and 3A) provides access by which an air hose can connect to the inlet port 61 of the upper body convective apparatus 60 in order to operate the apparatus for therapeutic warming. Warmed, pressurized air flows into and inflates the upper body convective apparatus 60, and exits through the permeable surface 64 toward a patient. The lower convective apparatus 70 with separately inflatable sections for therapeutic and comfort warming is disposed, supported, or constructed on the inside surface 43, in the lower portion 55, and is disposed longitudinally to the clinical garment 22, with the longitudinal axis 49 and extending from just above the lower edge 65 of the upper body convective apparatus 60 toward the lower hem 47. Preferably, the lower convective apparatus 70 has the construction illustrated in FIG. 3G with a dog-bone shaped comfort section 71 to provide comfort warming, and a second, separately-inflatable therapeutic section 72 that frames the comfort section 71 to provide therapeutic warming. An opening in the lower portion 55 of the clinical garment 22 (such as the flap 28 in FIGS. 2 and 3A) provides access by which an air hose can connect to the inlet port 74 of the comfort section 71 of the lower convective apparatus 70 to operate the comfort section 71 for comfort warming. Warmed, pressurized air flows into and inflates the comfort section 71, and exits through the permeable surface 79 of the section, toward a patient. An opening in the lower portion 55 of the clinical garment 22 (such as the flap 30 in FIG. 2) provides access by which an air hose can connect to a therapeutic section inlet port 85 of the therapeutic section 72 of the lower convective apparatus 70 to operate the section for therapeutic warming. Warmed, pressurized air flows into and inflates the therapeutic section 72, and exits through the permeable surface 86 of the section, toward a patient.

The comfort section 71 may be said to be "adapted" for comfort warming by virtue of an average or mean permeability of the permeable surface in the comfort section 71 that is lower than the average or mean permeability of the permeable surface in the therapeutic section 72. The lower average permeability in the corn fort section 71 accommodates a lower air volume entering the comfort section 71 from a relatively low capacity heater/blower unit, coupled by a smaller-diameter air hose to a smaller inlet port. Similarly, the therapeutic section 72 in the lower convective apparatus 70 may be said to be "adapted" for therapeutic warming by virtue of an average or mean permeability that is higher than the average or mean permeability in the permeable surface of the comfort section 71. The higher average permeability in the permeable surface of the therapeutic section accommodates a higher air volume entering the therapeutic section 72 from a relatively high capacity heater/blower unit, coupled by a larger-diameter air hose to a larger therapeutic section inlet port.

Each of the convective apparatuses 60 and 70 may be formed by joining two sheets of material with a closed impermeable seam formed by sealing the sheets of material around their peripheries and, in the lower convective apparatus, one or more additional closed impermeable seams to define separate comfort and therapeutic sections. One of the sheets is relatively impermeable and the other sheet is relatively more permeable to permit airflow therethrough. The sheets are further connected by discontinuous seals or stake points within the closed impermeable seams. The two sheets with which a convective apparatus is formed may be separate from the clinical garment 22, in which case the convective apparatuses are permanently or releasably attached, fixed, or adhered to the inside surface 43 of the clinical garment 22, with their permeable surfaces facing inwardly, toward a patient wearing the device 20. An exemplary construction in this regard is illustrated in FIGS. 1A and 1D and FIGS. 3A-3C of PCT publication WO 2003/086500. Alternately, the convective apparatuses may be formed or constructed integrally with a clinical garment 22 made of relatively impermeable material by attaching relatively permeable sheets to portions of the inside surface of the clinical garment 22. An exemplary construction in this regard is illustrated in FIGS. 1D and 1E and FIGS. 3D-3F of PCT publication WO 2003/086500.

According to the preferred construction of the warming device, each convective apparatus is formed or assembled separately from the clinical garment and then attached to its inside surface. The means by which the convective apparatuses may be so attached include taping, sewing, gluing, heat sealing, stapling, or welding, or any combination of these. Snaps, buttons, and hook and eye articles may also be used.

According to the present best mode of construction, each of the convective apparatuses is formed by heat sealing two sheets of material together. Each convective apparatus is formed with an impermeable polypropylene film and a permeable laminate sheet comprising a layer of nonwoven material on which a layer of polypropylene is extruded. The laminate sheet is made permeable by perforations formed therethrough. For the multi-section convective apparatus, the perforation densities are varied in order to provide the difference in permeability between the comfort and therapeutic sections. The polypropylene layer and polypropylene film are joined by an impermeable seal around their peripheries. Preferably, the impermeable seal is continuous. In the multi-section convective apparatus the polypropylene layer and polypropylene film are further joined by one or more additional seals continuous seals or stake points within the peripheral seal to form the comfort and therapeutic sections. Each convective apparatus is attached to a clinical garment by double-sided tape acting between the polypropylene film and the inside surface of the clinical garment so that the nonwoven material faces the patient. The reason for locating the polypropylene film on the inside surface of the clinical garment is to reduce the bulk and stiffness of the convective apparatus, thus making the warming device more comfortable to the patient.

When the warming device 20 is worn as shown in FIG. 2 for comfort warming, a convective apparatus may be connected to a heater/bower unit via an air hose to receive a stream of warmed pressurized air. The convective apparatus inflates in response to the stream of air and emits air through its permeable surface. The warming device 20 retains warmed air within the clinical garment 22 for comfort warming preoperatively. Preferably, although not necessarily, the comfort section 71 of the multi-section convective apparatus 70 is operated for comfort warming preoperatively.

A warming device includes a clinical garment with at least one convective apparatus supported on the inside of the garment. Pulling elements are provided to draw folded components of an upper body convective apparatus from sleeves of the clinical garment. A therapeutic section inlet port is provided in a location midway between the top and bottom edges of a lower, multi-section convective apparatus where the therapeutic section inlet port will be supported above a person's lower extremities when the lower portion of the warming device is used to therapeutically warm the lower extremities of a person.

Although the invention has been described with reference to the presently preferred embodiment, it should be understood that various modifications can be made without departing from the spirit of the invention. Accordingly, the invention is limited only by the following claims.

The invention claimed is:

1. A warming device, comprising:
a clinical garment having an inside surface, an upper portion with opposing sleeves, and a lower portion;
an upper body convective apparatus supported on the inside surface, in the upper portion;
the upper body convective apparatus including lateral extensions, each lateral extension having an end folded into a respective sleeve and a pulling element for pulling the folded end from the sleeve; and,
a lower convective apparatus supported on the inside surface, in the lower portion, and including separately inflatable sections.

2. The warming device of claim 1, wherein the upper body convective apparatus is disposed transversely across the upper portion, extending between the sleeves.

3. The warming device of claim 2, each end extending outwardly from a respective sleeve when unfolded.

4. The warming device of claim 2, each end having opposing side edges and an end edge, the pulling element of each end including at least one tab formed in a side edge where the end is creased when folded and pointing away from the end edge when the end is unfolded.

5. The warming device of claim 4, further including an indentation in the upper body convective apparatus between each tab and a side.

6. The warming device of claim 4, further including a peripheral line of weakness extending from each tab, along a side edge in which the tab is formed, and turning from the side edge to extend at least partially along the end edge.

7. The warming device of claim 6, wherein the upper body convective apparatus comprises an impermeable sheet of material joined to a permeable sheet of material by an impermeable seam and a plurality of stake seams inside the impermeable seam, each peripheral line of weakness being a trace of perforations in an end between a portion of the impermeable seam and a side edge and between the impermeable seam and a portion of the end edge.

8. The warming device of claim 6, further including a transverse nonlinear line of weakness in the upper body convective apparatus across each end to enable the separation of the end from the upper body convective apparatus.

9. The warming device of claim 1, wherein:
the lower convective apparatus is disposed longitudinally to the clinical garment and includes an upper edge near the upper body convective apparatus and a lower edge near a lower hem of the clinical garment; and,
one of the separately inflatable sections is a therapeutic warming section with an inlet port in a middle portion of the lower convective warming device, substantially midway between the upper edge and the lower edge.

10. The warming device of claim 9, wherein the inlet port is positioned near a side edge of the lower convective warming device.

11. The warming device of claim 10, wherein the lower convective apparatus comprises an impermeable sheet of material joined to a permeable sheet of material by an impermeable seam and one or more additional impermeable seams defining the separately inflatable sections, and the inlet port comprises a collar of stiff material with an opening through the sheet of impermeable material to receive the nozzle of an air hose.

12. The warming device of claim 11, further including an opening through the clinical garment aligned with the inlet port.

13. The warming device of claim 9, wherein the inlet port comprises a sleeve of material.

14. A warming device having a clinical garment and an upper body convective apparatus supported on an inside surface of the clinical garment and comprising lateral extensions, each lateral extension having an end folded into a respective sleeve of the clinical garment, side edge tie strips, and a pulling element for unfolding the folded end and separating the tie strips from side edges of the end.

15. The warming device of claim 14, wherein the upper body convective apparatus is disposed transversely across an upper portion of the clinical garment, between the sleeves.

16. The warming device of claim 15, each end extending outwardly from a respective sleeve when unfolded.

17. The warming device of claim 15, each end having opposing side edges and an end edge, the pulling element of each end including two opposing tabs, each tab formed in a side edge where the end is creased when folded and which points away from the end edge when the crease is unfolded.

18. The warming device of claim 17, further including an indentation in the upper body convective apparatus between each tab and a side.

19. The warming device of claim 17, each tie strip extending from a tab, along a side edge in which the tab is formed, and turning from the side edge to extend at least partially along the end edge.

20. The warming device of claim 19, wherein the upper body convective apparatus comprises an impermeable sheet of material joined to a permeable sheet of material by an impermeable seam, each tie strip being defined by a trace of perforations in an end between a portion of the impermeable seam and a side edge and between the impermeable seam and a portion of the end edge.

21. The warming device of claim 20, each trace of perforations curving between the side edge and the end edge.

22. The warming device of claim 20, each trace of perforations being defined between the impermeable seam and a peripheral seam.

23. The warming device of claim 20, each trace of perforations being terminated at a hole.

24. The warming device of claim 17, further including a transverse nonlinear line of weakness in the upper body convective apparatus across each end to enable the separation of the end from the upper body convective apparatus.

25. A warming device having a clinical garment and a lower convective apparatus supported on an inside surface in a lower garment portion of the clinical garment and having separately inflatable comfort and therapeutic warming sections, in which the lower convective apparatus includes an upper edge near a sleeve portion of the clinical garment and a lower edge near a lower hem of the clinical garment and the therapeutic warming section includes an inlet port in a middle portion of the lower convective warming device, substantially midway between the upper edge and the lower edge.

26. The warming device of claim 25, wherein the inlet port is positioned near a side edge of the lower convective warming device.

27. The warming device of claim 26, wherein the lower convective apparatus comprises an impermeable sheet of material joined to a permeable sheet of material by an impermeable seam and one or more additional impermeable seams defining the comfort and therapeutic warming sections, and the inlet port comprises a collar of stiff material with an opening through the sheet of impermeable material to receive the nozzle of an air hose.

28. The warming device of claim 27, further including an opening through the clinical garment aligned with the inlet port.

29. The warming device of claim 25, wherein the inlet port comprises a sleeve of material.

* * * * *

UNITED STATES PATENT AND TRADEMARK OFFICE
CERTIFICATE OF CORRECTION

| | | |
|---|---|---|
| PATENT NO. | : 8,097,031 B2 | Page 1 of 1 |
| APPLICATION NO. | : 12/386243 | |
| DATED | : January 17, 2012 | |
| INVENTOR(S) | : Thomas P Anderson | |

It is certified that error appears in the above-identified patent and that said Letters Patent is hereby corrected as shown below:

Page 2
Col. 1, U.S. Patent Documents, line 31, delete "Namemye" and insert
-- Namenye --, therefor.

Column 4
Line 16, delete "("The" and insert -- ("the --, therefor.

Column 9
Line 46, delete "1," and insert -- I, --, therefor.

Column 10
Line 53, delete "heater blower" and insert -- heater/blower --, therefor.
Line 54, delete "heater blower" and insert -- heater/blower --, therefor.

Signed and Sealed this
Eleventh Day of September, 2012

David J. Kappos
*Director of the United States Patent and Trademark Office*